US011278523B2

(12) United States Patent
Lin et al.

(10) Patent No.: US 11,278,523 B2
(45) Date of Patent: *Mar. 22, 2022

(54) INDOLINE DERIVATIVES FOR TREATMENT AND/OR PREVENTION OF FIBROSIS DISEASES

(71) Applicant: Taipei Medical University, Taipei (TW)

(72) Inventors: Chien Huang Lin, Taipei (TW); Jing-Ping Liou, Taipei (TW); Shiow-Lin Pan, Taipei (TW); Che-Ming Teng, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/771,476

(22) PCT Filed: Oct. 27, 2015

(86) PCT No.: PCT/US2015/057600
§ 371 (c)(1),
(2) Date: Apr. 27, 2018

(87) PCT Pub. No.: WO2017/074317
PCT Pub. Date: May 4, 2017

(65) Prior Publication Data
US 2018/0243264 A1    Aug. 30, 2018

(51) Int. Cl.
| *A61K 31/404* | (2006.01) |
| *A61P 1/16* | (2006.01) |
| *A61P 11/00* | (2006.01) |
| *A61P 13/12* | (2006.01) |
| *A61K 31/192* | (2006.01) |
| *A61P 17/00* | (2006.01) |
| *A61P 9/00* | (2006.01) |
| *A61K 31/4412* | (2006.01) |
| *A61P 1/00* | (2006.01) |
| *A61K 9/20* | (2006.01) |
| *A61K 9/48* | (2006.01) |
| *A61K 45/06* | (2006.01) |
| *A61K 31/435* | (2006.01) |
| *A61K 31/497* | (2006.01) |

(52) U.S. Cl.
CPC ............ *A61K 31/404* (2013.01); *A61K 9/20* (2013.01); *A61K 9/48* (2013.01); *A61K 31/192* (2013.01); *A61K 31/4412* (2013.01); *A61K 45/06* (2013.01); *A61P 1/00* (2018.01); *A61P 9/00* (2018.01); *A61P 11/00* (2018.01); *A61P 17/00* (2018.01); *A61K 31/435* (2013.01); *A61K 31/497* (2013.01); *A61K 2300/00* (2013.01)

(58) Field of Classification Search
CPC .. A61K 31/404; C07D 209/08; C07D 209/12; C07D 209/42

USPC ................. 415/415, 575; 548/490, 491, 469
See application file for complete search history.

(56) References Cited

U.S. PATENT DOCUMENTS

| 8,846,748 | B2 | 9/2014 | Chen et al. |
| 9,296,692 | B2* | 3/2016 | Chen .................... A61K 31/404 |
| 2011/0201643 | A1 | 8/2011 | Maier et al. |
| 2011/0245315 | A1 | 10/2011 | Chen et al. |
| 2015/0065552 | A1* | 3/2015 | Chen .................... A61K 31/404 |
| | | | 514/418 |
| 2015/0368195 | A1* | 12/2015 | Liou .................... C07D 209/08 |
| | | | 514/419 |
| 2016/0230226 | A1 | 8/2016 | Abbas et al. |

FOREIGN PATENT DOCUMENTS

| WO | 2014070983 A1 | 5/2014 |
| WO | 2015077685 A1 | 5/2015 |

OTHER PUBLICATIONS

Huang et al. PLOS One, 7 (8), e43645, pp. 1-11, published Aug. 22, 2012.*
Definition of prevent, Princeton University "About WordNet." WordNet. Princeton University. 2010. <http://wordnet.princeton.edu>, accessed Sep. 18, 2012.*
Fingerlin et al. Nature Genetics 2013, 45 (6), 613-620.*
Friedman et al. Science Translational Medicine 2013, 5 (167), 167sr1, pp. 1-17.*
Sanders et al. Eur. Respir. J. 2014, 43, 1448-1458.*
Huang et al. PLOS One 2012, 7 (8), e43645-, pp. 1-11, published Aug. 22, 2012.*
Pang, M., et al., "Histone Deacetylase: A Potential Therapeutic Target for Fibrotic Disorders," The Journal of Pharmacology and Experimental Therapeutics, 2010, vol. 335, No, 2, pp. 266-272.
International Search Report and Written Opinion, from PCT/US15/57600, dated Jan. 14, 2016.
Yoshikawa et al., "Inhibition of Histone Deacetylase Activity Suppresses Epithelial-to-Mesenchymal Transition Induced by TGF-beta1 in Human Renal Epithelial Cells", J Am Soc Nephrol 18: 58-65, 2007.
Extended European Search Report dated May 23, 2019 in corresponding EP application 15907425.1, 11 pages.
Pang M et al.: "Histone Deacetylase: A Potential Therapeutic Target for Fibrotic Disorders," Journal of Pharmacology and Experimental Therapeutics, (Aug. 18, 2010), vol. 335, No. 2, pp. 266-272.
Hsieh et al., "Preclinical anti-arthritic study and pharmacokinetic properties of a potent histone deacetylase inhibitor MPT0G009," Cell Death & Disease, (Apr. 1, 2014), vol. 5, No. 4, pp. e1166-e1166; 10 pages.
Huang et al., "Anticancer Activity of MPT0E028, a Novel Potent Histone Deacetylase Inhibitor, in Human Colorectal Cancer HCT116 Cells In Vitro and In Vivo", PLOS One, (Aug. 22, 2012), vol. 7, No. 8, p. e43645; 11 pages.

(Continued)

*Primary Examiner* — Irina Neagu
(74) *Attorney, Agent, or Firm* — Duane Morris LLP

(57) ABSTRACT

The invention relates to the use of Indoline derivatives, and their effective dose in the prevention and/or treatment of fibrosis diseases. The compound can effectively prevent and/or treat a fibrosis disease without cytotoxicity or genotoxicity.

12 Claims, 6 Drawing Sheets

(56) References Cited

OTHER PUBLICATIONS

Lee et al., "1-Arylsulfonyl-5-( N-hydroxyacrylamide)indolines Histone Deacetylase Inhibitors Are Potent Cytokine Release Suppressors," CHEMBIOCHEM, (Jun. 20, 2013), vol. 14, No. 10, pp. 1248-1254.
Lee et al., "Effect of C7-substitution of 1-arylsulfonyl-5-(N-hydroxyacrylamide)indolines on the selectivity towards a subclass of histone deacetylases," Organic & Biomolecular Chemistry, (2014), vol. 12, No. 44, pp. 8966-8976.
Office Action in Japan Counterpart Application No. 2018-521343, dated Jul. 10, 2020, in 7 pages; Machine translation provided.

* cited by examiner

INDOLINE DERIVATIVES FOR TREATMENT AND/OR PREVENTION OF FIBROSIS DISEASES

CROSS-REFERENCE TO RELATED APPLICATIONS

This application is a § 371 national stage entry of International Application No. PCT/US2015/057600, filed Oct. 27, 2015, the entire contents of which are incorporated herein by reference.

FIELD OF THE INVENTION

The invention relates to a method or use for treating and/or preventing fibrosis disease. Particularly, the method uses indoline derivatives to treat and/or prevent fibrosis diseases without cytotoxicity and genotoxicity.

BACKGROUND OF THE INVENTION

Fibrosis is the formation of excess fibrous connective tissue in an organ or tissue in a reparative or reactive process, e.g., healing, usually because of injury or long-term inflammation. Fibrosis causes the affected tissues to harden and/or swell and reduces the flow of fluids through these tissues. As a result, a number of tissues may have fibrosis and tissues with fibrosis may not be able to function properly. For example, hepatic fibrosis is overly exuberant wound healing in which excessive connective tissue builds up in the liver. Chronic liver diseases can lead to liver fibrosis with the principle causes chronic viral hepatitis B and alcoholic liver disease. Pulmonary fibrosis (literally "scarring of the lungs") is a respiratory disease in which scars are formed in the lung tissues, leading to serious breathing problems. Scar formation, the accumulation of excess fibrous connective tissue (the process called fibrosis), leads to thickening of the walls, and causes reduced oxygen supply in the blood. As a consequence patients suffer from perpetual shortness of breath. Renal fibrosis is the inevitable consequence of an excessive accumulation of extracellular matrix that occurs in virtually every type of chronic kidney disease. Intestinal fibrosis is a common complication of inflammatory bowel disease (IBD) and can occur in both ulcerative colitis (UC) and Crohn's disease (CD), but is much more prevalent in CD. Fibrosis can also occur in the heart, e.g., cardiac fibrosis can occur as a thickening of a heart valve.

Histone deacetylases (HDACs) are classified according to four categories: class I (HDAC1, 2, 3, and 8); class IIa (HDAC4, 5, 7, and 9) and class IIb (HDAC6 and 10); class III (SIRT1-7); and class IV (HDAC11). These are involved in the post-translational modifications of core histone and nonhistone proteins. U.S. Pat. No. 8,846,748 discloses certain indolyl or indolinyl hydroxamate compounds as HDAC inhibitors having potent anticancer activity. Masahiro Yoshikawa et al. indicate that HDAC inhibitors prevent fibrosis in the liver, skin and lung, but most of their underlying mechanisms remain to be elucidated, and suggests that TSA, an HDAC inhibitor, induces several inhibitory factors of TGF-beta 1 signals, such as Id2 and BMP-7, in human RPTEC (Masahiro Yoshikawa et al., *J Am Soc Nephrol* 18: 58-65, 2007). Maoyin Pang and Shougang Zhuang indicate that development and progression of some chronic diseases are characterized by fibrosis, including chronic kidney disease, cardic hypertrophy and idiopathic pulmonary fibrosis (Maoyin Pang and Shougang Zhuang, *The Journal of Pharmacology and Experimental Therapeutics*, Vol. 355, No. 2, pp. 266-272, 2010).

However, there are very few HDAC inhibitors that have been sufficiently developed to identify a potential candidate for fibrosis. Therefore, there is still a need to develop an anti-fibrosis drug.

SUMMARY OF THE INVENTION

The invention provides a method for prevention and/or treatment of a fibrosis disease in a subject, comprising administering an effective amount of a compound described herein as an active ingredient to the subject. Preferably, the effective amount is n a range of about 1.5 mg/kg/day to about 20 mg/kg/day to the subject. In some embodiments, the effective amount of the active ingredient ranges from about 1.5 mg/kg/day to about 15 mg/kg/day, about 1.5 mg/kg/day to about 13 mg/kg/day, about 1.5 mg/kg/day to about 12 mg/kg/day, about 1.5 mg/kg/day to about 10 mg/kg/day, about 2.0 mg/kg/day to about 20 mg/kg/day, about 2.0 mg/kg/day to about 15 mg/kg/day, about 2.0 mg/kg/day to about 13 mg/kg/day or about 2.0 mg/kg/day to about 12 mg/kg/day, about 5 mg/kg/day to about 20 mg/kg/day, about 5 mg/kg/day to about 15 mg/kg/day or about 5 mg/kg/day to about 10 mg/kg/day. In some embodiments, the active ingredient of the method of the invention is further co-administered with a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101). In some embodiments, the fibrosis disease is skin fibrosis, lung fibrosis, renal fibrosis, liver fibrosis, intestinal fibrosis, cystic fibrosis, cardiac fibrosis, uterine leiomyoma or adenomyosis. In a further embodiment, the lung fibrosis is idiopathic pulmonary fibrosis.

The invention also provides a pharmaceutical composition comprising a daily dose of 3-(1-benzenesulfonyl-2,3-dihydro-1H-indol-5-yl)-N-hydroxyacrylamide or a pharmaceutically acceptable salt, solvate or prodrug as an active ingredient in a range from about 100 mg to about 1,400 mg in one or more unit dosage forms

DETAILED DESCRIPTION OF THE INVENTION

Figure 1A:
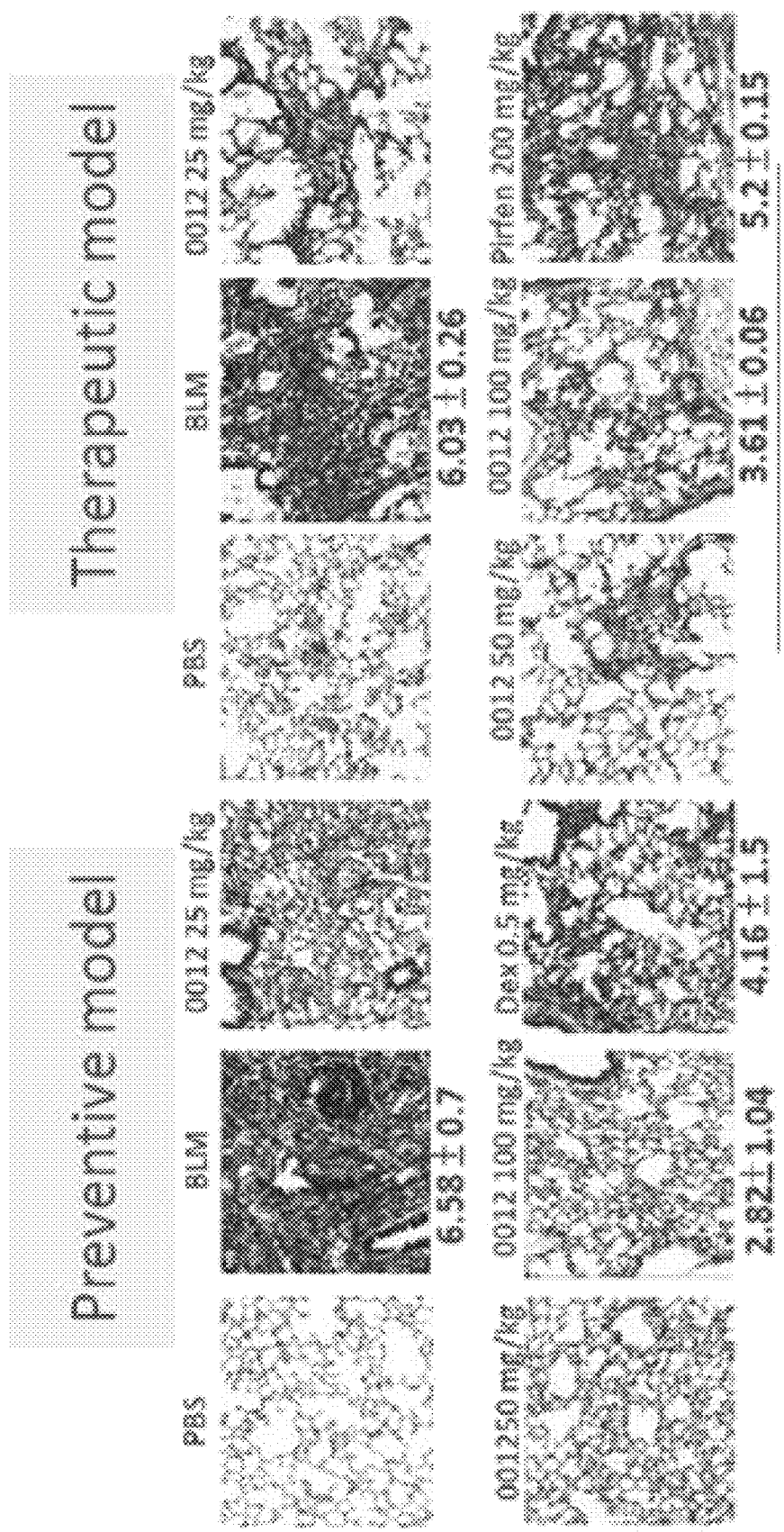
FIGS. 1(A), (B) and (C) show the antifibrotic effects of TMU-C-0012, dexamethasone and pirfenidone on bleomydcin-induced pulmonary fibrosis in mice. In the preventive model, the results show that TMU-C-0012 inhibits BLM-induced lung fibrosis in dose-dependent manner (A), and the efficacy of TMU-C-0012 in the inhibition is higher than dexamethasone (B). In the therapeutic model, the results show that TMU-C-0012 inhibits BLM-induced lung fibrosis in dose-dependent manner (A), and the efficacy of TMU-C-0012 in inhibition is higher than pirfenidone (C).

The invention is, at least in part, based on the discovery of using an indoline derivative and its effective dose in the prevention and/or treatment of fibrosis diseases. The compound can effectively prevent and/or treat a fibrosis disease without cytotoxicity or genotoxicity.

As used herein, except where the context requires otherwise, the term "comprise" and variations of the term, such as "comprising," "comprises" and "comprised" are not intended to exclude other additives, components, integers or steps.

As used herein, except where the context requires otherwise, the method steps disclosed are not intended to be limiting nor are they intended to indicate that each step is essential to the method or that each step must occur in the order disclosed.

As used herein, the use of "or" means "and/or" unless stated otherwise. In the context of a multiple dependent claim, the use of "or" refers back to more than one preceding independent or dependent claim in the alternative only.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal and ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "prodrug" refers to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides.

The terms "administer," "administering," or "administration," as used herein, refers to implanting, absorbing, ingesting, injecting, inhaling, or otherwise introducing an inventive compound, or a pharmaceutical composition thereof, in or on a subject.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "pharmaceutically acceptable carrier" refers to a solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentration employed, and is compatible with other ingredients of the formulation. Pharmaceutically acceptable carriers are determined in part by the particular composition being administered, as well as by the particular method used to administer the composition.

As used herein, the term "subject" is defined herein to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

As used herein, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agents, after the diagnosis or onset of symptoms of the particular disease.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of a compound or an antibody or dosage form provided herein, with or without one or more other additional active agents, prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment."

As used herein, the terms "co-administration" and "in combination with" include the administration of two or more therapeutic agents simultaneously, concurrently, separately or sequentially within no specific time limits unless otherwise indicated. In one embodiment, the therapeutic agents are in the same composition or unit dosage form. In other embodiments, the therapeutic agents are in separate compositions or unit dosage forms.

In one aspect, the invention provides a method for prevention and/or treatment of a fibrosis disease in a subject, comprising administering an effective amount of a compound of Formula (I) or a pharmaceutically acceptable salt, solvate or prodrug thereof as an active ingredient to a subject;

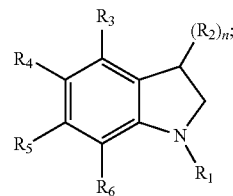

(I)

wherein n is 0, 1, or 2;
$R_1$ is $SO_2R_a$, in which $R_a$ is alkenyl, alkynyl, phenyl, heteroaryl, cycloalkyl, cycloalkenyl, heterocycloalkyl, or heterocycloalkenyl;
$R_2$ is alkyl, alkenyl, alkynyl, aryl, heteroaryl, cycloalkyl, cycloalkenyl, heterocycloalkyl, heterocycloalkenyl, halo, cyano, nitro, $OR_b$, $SR_b$, $S(O)R_b$, $NHC(O)-CH=CH-C(O)R_b$, $NHC(O)-CH=CH-C(O)NR_cR_d$, $SO_2NR_cR_d$, $OC(O)R_b$, $C(O)NR_cR_d$, $NR_cR_d$, $NHC(O)R_b$, $NHC(O)NR_cR_d$, or $NHC(S)R_c$, in which each of $R_b$, $R_c$, and $R_d$, independently, is H, hydroxy, alkoxy, aryloxy, heteroaryloxy, alkyl, alkenyl, alkynyl, aryl, heteroaryl, cycloalkyl, cycloalkenyl, heterocycloalkyl, or heterocycloalkenyl; and each of $R_3$, $R_4$, $R_5$, and $R_6$, independently is, H, alkyl, alkenyl, alkynyl, aryl, heteroaryl, cycloalkyl, cycloalkenyl, heterocycloalkyl, heterocycloalkenyl, halo, cyano, nitro, $OR_b$, $SR_b$, $S(O)R_b$, $CH=CH-C(O)NR_cR_d$, $NHC(O)-CH=CH-C(O)R_b$, $NHC(O)-CH=CH-C(O)NR_cR_d$, $SO_2NR_cR_d$, $OC(O)R_b$, $C(O)NR_cR_d$, $NR_cR_d$, $NHC(O)R_b$, $NHC(O)NR_cR_d$, or $NHC(S)R_c$, in which each of $R_b$, $R_c$, and $R_d$, independently, is H, hydroxy, alkoxy, aryloxy, heteroaryloxy, alkyl, alkenyl, alkynyl, aryl, heteroaryl, cycloalkyl, cycloalkenyl, heterocycloalkyl, or heterocycloalkenyl.

In some embodiments, $R_4$ is $CH=CH-C(O)NR_cR_d$, $NHC(O)-CH=CH-C(O)R_b$, or $NHC(O)-CH=CH-C(O)NR_cR_d$; Preferably, $R_4$ is $C(O)NHOH$, $CH=CH-C(O)NHOH$, $NHC(O)-CH=CH-C(O)OH$, or $NHC(O)-CH=CH-C(O)NHOH$; more preferably, $R_4$ is $CH=CH-C(O)NHOH$.

In some embodiments, $R_1$ is $SO_2R_a$ and $R_a$ is heteroaryl or phenyl optionally substituted with halo, hydroxyl, alkoxyl, amino, cyano, or nitro.

In some embodiments, $R_2$ is $NHC(O)-CH=CH-C(O)R_b$ or $NHC(O)-CH=CH-C(O)NR_cR_d$; and $R_3$, $R_5$, and $R_6$ is independently $CH=CH-C(O)NR_cR_d$, $NHC(O)-CH=CH-C(O)R_b$, or $NHC(O)-CH=CH-C(O)NR_cR_d$.

In some further embodiments, $R_2$ is $NHC(O)-CH=CH-C(O)OH$, or $NHC(O)-CH=CH-C(O)NHOH$; $R_3$, $R_5$, and $R_6$ is independently $CH=CH-C(O)NHOH$, $NHC(O)-CH=CH-C(O)OH$, or $NHC(O)-CH=CH-C(O)NHOH$; $R_1$ is $SO_2R_a$ wherein $R_a$ is heteroaryl or phenyl optionally substituted with halo, hydroxyl, alkoxyl, amino, cyano, or nitro.

In a further embodiment, the compound of formula (I) is selected from the group consisting of:

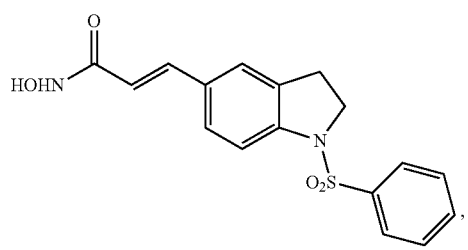

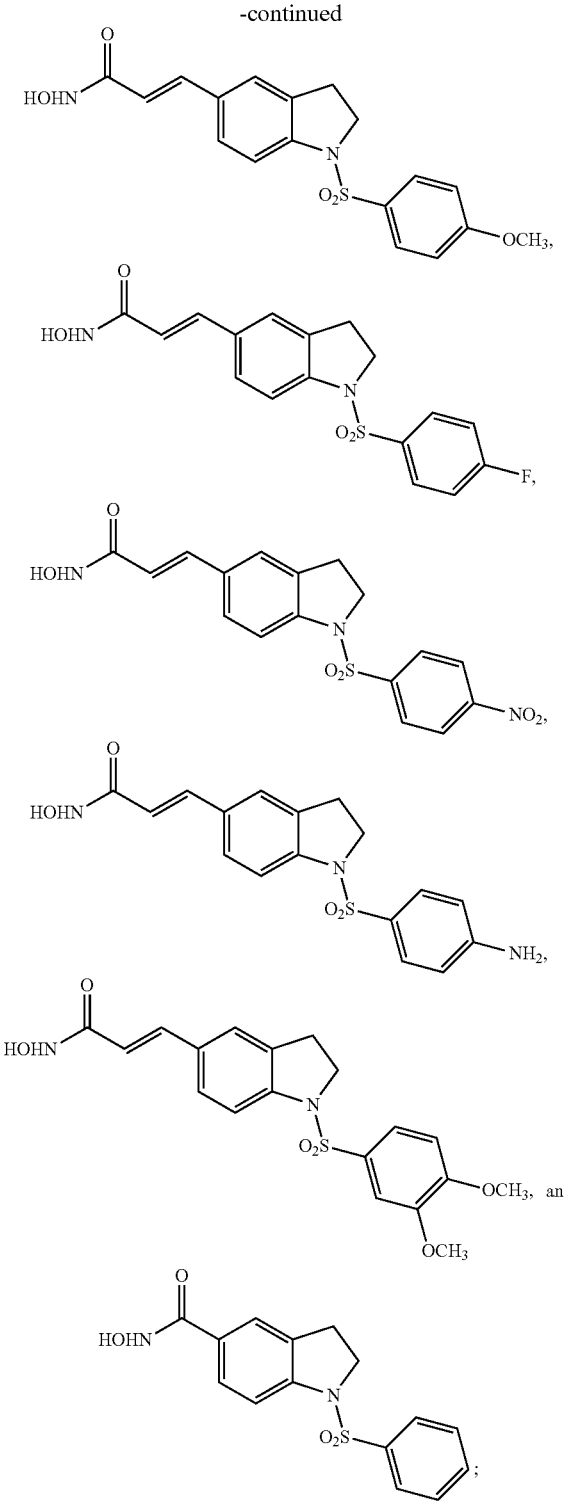
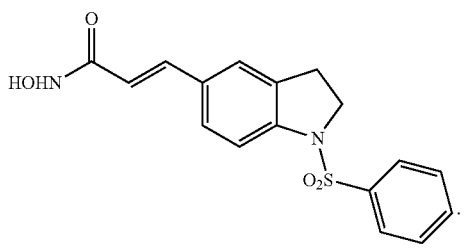

or a pharmaceutically acceptable salt, solvate or prodrug thereof.

In a further embodiment, the compound of Formula (I) is 3-(1-benzenesulfonyl-2,3-dihydro-1H-indol-5-yl)-N-hydroxyacrylamide or a pharmaceutically acceptable salt, solvate or prodrug thereof. The structure of 3-(1-benzenesulfonyl-2,3-dihydro-1H-indol-5-yl)-N-hydroxyacrylamide is shown as follows.

In one embodiment, the effective amount is in a range of about 1.5 mg/kg/day to about 20 mg/kg/day. In another embodiment, the effective amount for a human is in a range of about 2.0 mg/kg/day to about 15 mg/kg/day. On the other hand, the invention also provides a use of an effective amount of a compound described herein or a pharmaceutically acceptable salt, solvate or prodrug as an active ingredient for the manufacture of a medicament for prevention and/or treatment of a fibrosis disease.

The compounds of the Formula (I) as described herein and their preparation have been disclosed in U.S. Pat. No. 8,846,748, which is incorporated herein by reference.

In some further embodiments, the effective amount of the active ingredient used in the invention ranges from about 1.5 mg/kg/day to about 15 mg/kg/day, about 1.5 mg/kg/day to about 13 mg/kg/day, about 1.5 mg/kg/day to about 12 mg/kg/day, about 1.5 mg/kg/day to about 10 mg/kg/day, about 2.0 mg/kg/day to about 20 mg/kg/day, about 2.0 mg/kg/day to about 15 mg/kg/day, about 2.0 mg/kg/day to about 13 mg/kg/day or about 2.0 mg/kg/day to about 12 mg/kg/day, about 5 mg/kg/day to about 20 mg/kg/day, about 5 mg/kg/day to about 15 mg/kg/day or about 5 mg/kg/day to about 10 mg/kg/day. In a further embodiment, the effective amount used in the invention is about 2.3 mg/kg/day to about 11 mg/kg/day.

For the treatment of a fibrosis disease, the effective amount of the active ingredient ranges from about 5 mg/kg/day to about 20 mg/kg/day, about 5 mg/kg/day to about 18 mg/kg/day, about 5 mg/kg/day to about 15 mg/kg/day, about 5 mg/kg/day to about 13 mg/kg/day, about 5 mg/kg/day to about 11 mg/kg/day or about 5 mg/kg/day to about 10 mg/kg/day.

For the prevention of a fibrosis disease, the effective amount of the active ingredient ranges from about 1.5 mg/kg/day to about 10 mg/kg/day, about 1.5 mg/kg/day to about 8 mg/kg/day, about 2 mg/kg/day to about 10 mg/kg/day, about 4.0 mg/kg/day to about 8 mg/kg/day, or about 6.0 mg/kg/day to about 8.0 mg/kg/day.

In one embodiment, the active ingredient of the invention is further co-administered with a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101). In a further embodiment, the co-administration is simultaneous, separate or sequential administration.

In some embodiments, the fibrosis disease is skin fibrosis, lung fibrosis, renal fibrosis, liver fibrosis, intestinal fibrosis, cystic fibrosis, cardiac fibrosis, uterine leiomyoma or adenomyosis. In a further embodiment, the lung fibrosis is idiopathic pulmonary fibrosis. In another further embodiment, the method for treatment of lung fibrosis further comprises a co-administered therapy with lung transplantation, hyperbaric oxygen therapy (HBOT), pulmonary rehabilitation.

In another aspect, the invention provides a pharmaceutical composition comprising a daily dose of the compound of Formula (I) as described herein or a pharmaceutically acceptable salt, solvate or prodrug as an active ingredient in a range from about 100 mg to about 1,400 mg in one or more unit dosage forms. In one embodiment, the pharmaceutical composition of the invention comprises a daily dose ranging from about 140 mg to about 1,050 mg.

In some embodiments, the pharmaceutical composition of the invention is in one or more capsule forms or tablet forms. In a further embodiment, the pharmaceutical composition of the invention comprises about 100 mg to about 300 mg, about 150 mg to about 300 mg, about 150 mg to about 250 mg, about 200 mg to 250 mg, about 220 mg to about 280 mg, about 220 mg to about 250 mg or about 200 mg to about 220 mg of the active ingredient in a single tablet; preferably, about 200 mg or 220 mg in a single tablet. In another further embodiment, the pharmaceutical composition of the invention comprises about 100 mg to about 500 mg, about 150 mg to about 500 mg, about 180 mg to about 500 mg, about 200 mg to about 500 mg, about 150 mg to about 350 mg, about 150 mg to about 300 mg, about 200 mg to about 400 mg, about 200 mg to about 400 about 350 mg, about 200 mg to about 300 mg, about 250 mg to about 500 mg, about 250 mg to about 400 mg, about 250 mg to about 350 mg or about 250 mg to about 300 mg of the active ingredient in a single capsule; preferably, about 250 mg of the active ingredient in a single capsule.

In one embodiment, the pharmaceutical composition of the invention comprises a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101).

While it may be possible for the compounds of the invention to be administered as the raw chemical, it is also possible to present them as a pharmaceutical formulation. Accordingly, the present invention provides a pharmaceutical formulation or composition comprising a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Formulations may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration, although the most suitable route may depend, for example, upon the condition and disorder of the recipient. Oral administration is a preferred route. The formulations may conveniently be presented in unit dosage form and may be prepared by any of the methods well known in the art of pharmacy. All methods include the step of bringing into association a compound of the present invention or a pharmaceutically acceptable salt, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds or compositions of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds or compositions of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

Dosage regimens can be adjusted to provide the optimum therapeutic response. For example, several divided dosages may be administered daily or the dosage may be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labelled or accompanied by a label indicating the intended method of treatment.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Example 1

Ames Test for Genotoxicity of 3-(1-Benzenesulfonyl-2,3-dihydro-1H-indol-5-yl)-N-hydroxyacrylamide The compound, 3-(1-Benzenesulfonyl-2,3-dihydro-1H-indol-5-yl)-N-hydroxyacrylamide (hereafter referred to as "TMU-C-0012") was evaluated using the Ames test to assess mutagenic potential. Two histidine auxotrophic mutants (TA98 and TA100) of *Salmonella typhimurium* were used. Test strains were obtained from the frozen working stock vial and thawed at room temperature. A 0.2 mL aliquot was inoculated into 25 mL nutrient broth medium and then incubated at 35-37° C. with shaking (120 rpm) for 16-18 hours. The test substance was dissolved in DMSO with 10-fold dilutions to obtain 4 stock concentrations at 30,000, 3,000, 300 and 30 μg/mL. Rat liver microsome enzyme homogenate (S9) mixture was prepared containing 8 mM $MgCl_2$, 33 mM KCl, 4 mM NADP, 5 mM glucose-6-phosphate, 100 mM $NaH_2PO_4$ (pH 7.4) and 4% (v/v) Aroclor 1254-induced male rat liver microsome enzyme homogenate (S9). A 0.2 mL aliquot of test compound stock solution was combined with 0.1 mL strain culture and with 0.5 mL rat liver enzyme homogenate (S9) mixture or 0.5 mL PBS, and then the mixture was incubated at 35-37° C. with shaking (120 rpm) for 20 min. Molten top agar (2 mL containing 0.05 mM histidine and 0.05 mM biotin) was added, and then the mixture was poured onto the surface of a minimal glucose agar plate (30 mL of bottom agar per petri plate) to obtain final test substance concentrations at 3000, 300, 30 and 3 μg/plate. The plates were incubated at 37° C. for 72 hours, and then the numbers of His+ revertant colonies were counted. Treatments resulting in a three-fold increase (≥3×) in revertant colonies compared to the vehicle control were considered mutagenic. Treatments that reduced the colony counts to ≤50% of the vehicle control were considered cytotoxic. Assays were performed in triplicate.

The following table shows the Ames test results, which show that the genotoxicity of the compound, TMU-C-0012, is negative.

| | | TA98 | | | | TA100 | | | |
|---|---|---|---|---|---|---|---|---|---|
| | | With S9 | | Without S9 | | With S9 | | Without S9 | |
| Treatment | Concentration | Mutagenicity | Cytotoxicity | Mutagenicity | Cytotoxicity | Mutagenicity | Cytotoxicity | Mutagenicity | Cytotoxicity |
| TMU-C-0012 | 3000 μg/plate | — | — | — | — | — | — | — | — |
| | 300 μg/plate | — | — | — | — | — | — | — | — |
| | 30 μg/plate | — | — | — | — | — | — | — | — |
| | 3 μg/plate | — | — | — | — | — | — | — | — |

—: No significant mutagenicity or cytotoxicity
+: Significant mutagenicity or cytotoxicity

Example 2

In Vitro Mammalian Cell Micronucleus Assay

The in vitro micronucleus (MNvit) assay uses cultured human cells to provides a comprehensive basis for investigating chromosome damaging potential in vitro by detecting both aneugens and clastogens. The assay was performed with the actin polymerisation inhibitor cytochalasin B (Cyto B), followed the OECD Guideline for Testing of Chemicals—*TG 487, In Vitro Mammalian Cell Micronucleus Test (MNvit)* (2014).

The following table shows the results of the assay and exhibits that the genotoxicity of the compound, TMU-C-0012, is negative.

| Compound | Test Concentration (M) | Scored Cells | % Cytotoxicity CBPI Index | % Cytotoxicity Cell Numbers | % Micronucleated Cells | t-Test p-Value | Test Result | Flat |
|---|---|---|---|---|---|---|---|---|
| Micronucleus (CHO + S9, HCA) | | | | | | | | |
| TMU-C-0012 | 3.1E−05 | 2014 | 41.5 | 19.1 | 1.64 | 0.1771 | — | |
| TMU-C-0012 | 6.3E−05 | 1676 | 47.3 | 31.9 | 1.26 | 0.4432 | — | |
| TMU-C-0012 | 1.3E−04 | 1176 | 57.4 | 37.6 | 1.45 | 0.2904 | — | |
| TMU-C-0012 | 2.5E−04 | 727 | 62.2 | 51.8 | 1.76 | 0.1849 | — | |

-continued

| | | | | | | | |
|---|---|---|---|---|---|---|---|
| TMU-C-0012 | 5.0E−04 | 401 | 68.8 | 61.7 | 1.94 | 0.1675 | — | PREC CYTO |
| TMU-C-0012 | 1.0E−03 | | | | | | | PREC CYTO |
| Micronucleus (CHO + S9, HCA) | | | | | | | |
| TMU-C-0012 | 7.8E−06 | 2010 | 26.7 | 42.2 | 1.29 | 0.0209 | — |
| TMU-C-0012 | 1.6E−05 | 1214 | 53.1 | 60.4 | 1.35 | 0.0174 | — |
| TMU-C-0012 | 3.1E−05 | 727 | 58.8 | 69.0 | 1.25 | 0.2140 | — |
| TMU-C-0012 | 6.3E−05 | | | | | | | CYTO |
| TMU-C-0012 | 1.3E−04 | | | | | | | CYTO |
| TMU-C-0012 | 2.5E−04 | | | | | | | CYTO |
| TMU-C-0012 | 5.0E−04 | | | | | | | PREC CYTO |
| TMU-C-0012 | 1.0E−03 | | | | | | | PREC CYTO |

Genetic Toxocity
Reference Compound Data

| | Test Concentration (M) | Scored Cells | % Cytotoxicity CBPI Index | % Cytotoxicity Cell Numbers | % Micronucleated Cells | t-Test p-Value | Test Result |
|---|---|---|---|---|---|---|---|
| Micronucleus (CHO + S9, HCA) | | | | | | | |
| Control + S9 | | 2154 | 39.0 | 52.5 | 1.19 | N/A | N/A |
| Cyclophosphamide | 3.6E−05 | 756 | 46.3 | 54.6 | 5.31 | 0.0007 | + |
| Micronucleus (CHO + S9, HCA) | | | | | | | |
| Control + S9 | | 4008 | 0.1 | 0.0 | 0.70 | N/A | N/A |
| Mitomycin C | 3.0E−07 | 2007 | 4.0 | 21.9 | 4.38 | 0.0000 | + |

PREC: Precipitate observable under the microscope.
CYTO: High cytotoxicity resulting in an insufficient number of scored cells (≥80% cytotoxicity)
Notes:
'+' $p < 0.05$ by t-test and % of micronucleated cells at least 3-fold higher than background levels.
'+/−' $p < 0.05$ by t-test and % of micronucleated cells at least 2-fold higher than background levels.

Example 3

In Vivo Efficacy: Bleomycin (BLM)-Induced Lung Fibrosis Mice Model Assay

In preventive model, C57BL/6JNarl mice (8 weeks) were treated with bleomycin (BLM, 0.05 U/50 μl) or PBS (50 μl) by endotracheal administration. TMU-C-0012 (25, 50, 100 mg/kg/day, q.d.) and dexamethasone (0.5 mg/kg/day, q.d.) were administered orally to bleomycin-treated mice from 1 to 21 days after BLM treatment. On day 21, the mice were sacrificed and, the histologic analysis of lung tissue was performed by hematoxylin-eosin (H&E) staining (original magnification, ×100). In therapeutic model, C57BL/6JNarl mice (8 weeks) were treated with bleomycin (BLM, 0.05 U/50 μl) or PBS (50 μl) by endotracheal administration. TMU-C-0012 (25, 50, 100 mg/kg/day, q.d.) and pirfenidone (200 mg/kg/day, q.d.) were administered orally to bleomycin-treated mice from 10 to 38 days after BLM treatment. On day 39, the mice were sacrificed, and the histologic analysis of lung tissue was performed by hematoxylin-eosin (H&E) staining (original magnification, ×100).

Figure 1B:
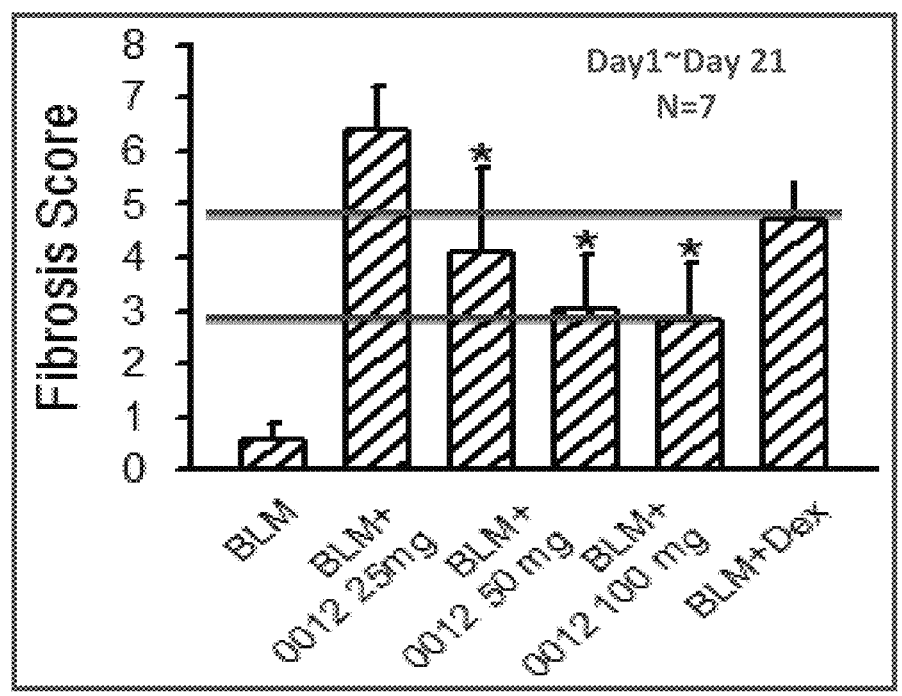
Figure 1C:
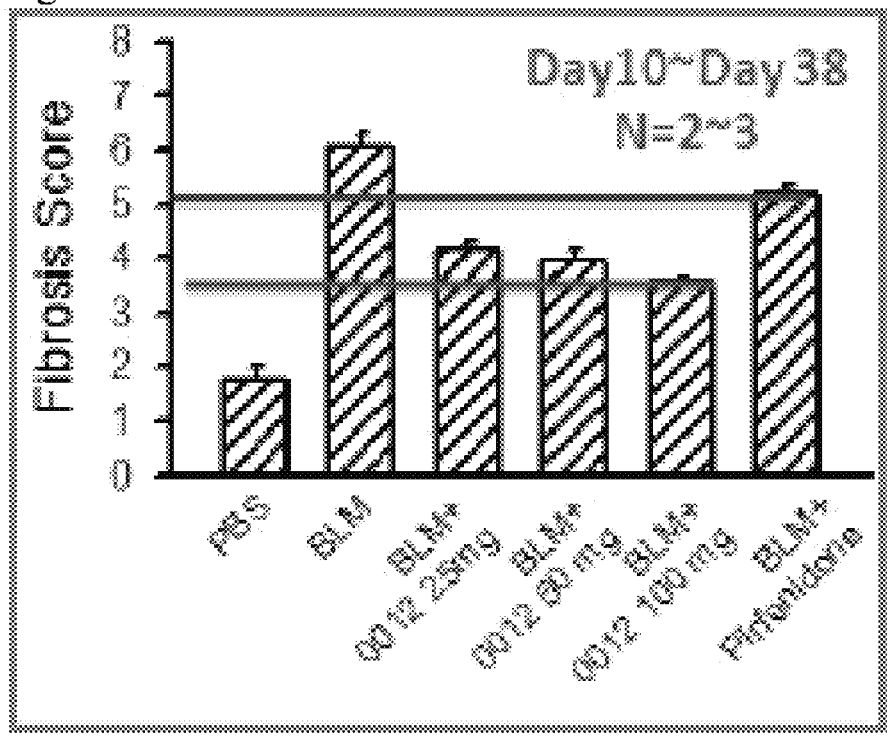

FIGS. 1A, 1B and 1C show the antifibrotic effects of TMU-C-0012, dexamethasone and pirfenidone on bleomydcin-induced pulmonary fibrosis in mice. In the preventive model, the results show that TMU-C-0012 inhibits BLM-induced lung fibrosis in a dose-dependent manner (see FIG. 1(A)), and the efficacy of TMU-C-0012 in the inhibition is higher than dexamethasone (see FIG. 1(B)). In the therapeutic model, the results show that TMU-C-0012 inhibits BLM-induced lung fibrosis in a dose-dependent manner (see FIG. 1(A)), and the efficacy of TMU-C-0012 in inhibition is higher than pirfenidone (see FIG. 1(C)).

Figure 2:
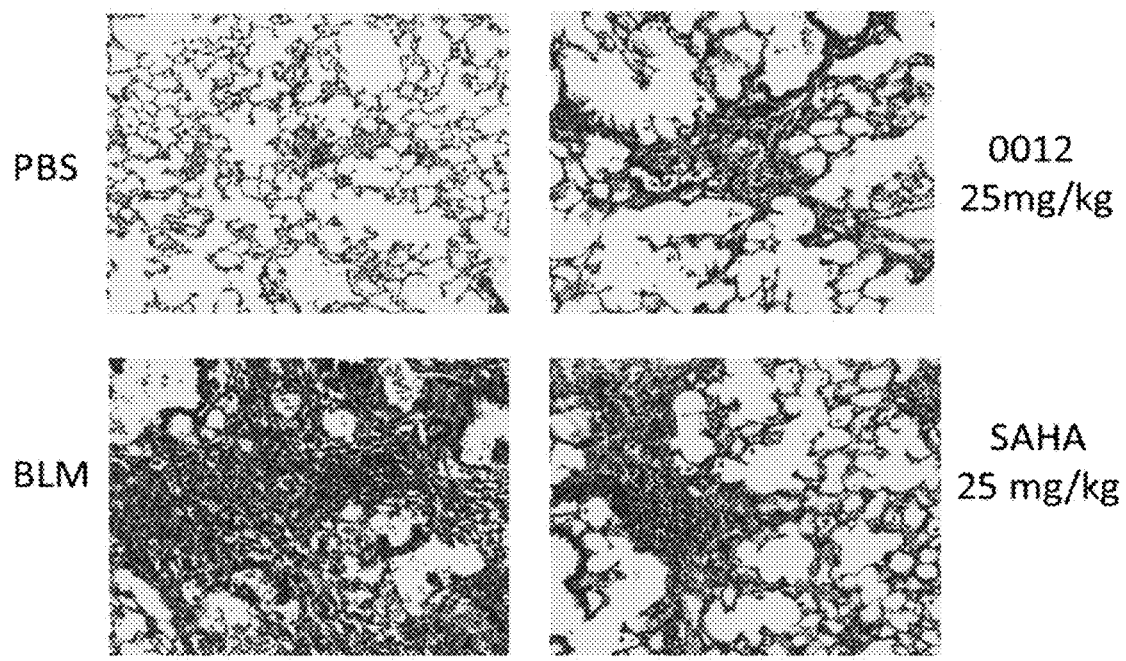
FIG. 2 shows the antifibrotic effects of TMU-C-0012 and SAHA on bleomydcin-induced pulmonary fibrosis in mice.

In addition, C57BL/6JNarl mice (8 weeks) were treated with bleomycin (BLM, 0.05 U/50 μl) or PBS (50 μl) by endotracheal administration. TMU-C-0012 (25 mg/kg/day, q.d.) and SAHA (25 mg/kg/day, q.d.) were administered orally to bleomycin-treated mice from 10 to 38 days after BLM treatment. On day 39, the mice were sacrificed, and the histologic analysis of lung tissue was performed by hematoxylin-eosin (H&E) staining (original magnification, ×100). FIG. 2 shows the antifibrotic effects of TMU-C-0012 and SAHA on bleomydcin-induced pulmonary fibrosis in mice.

Example 4

In Vivo Efficacy: OVA Lung Fibrosis Mice Model Assay

Figure 3:
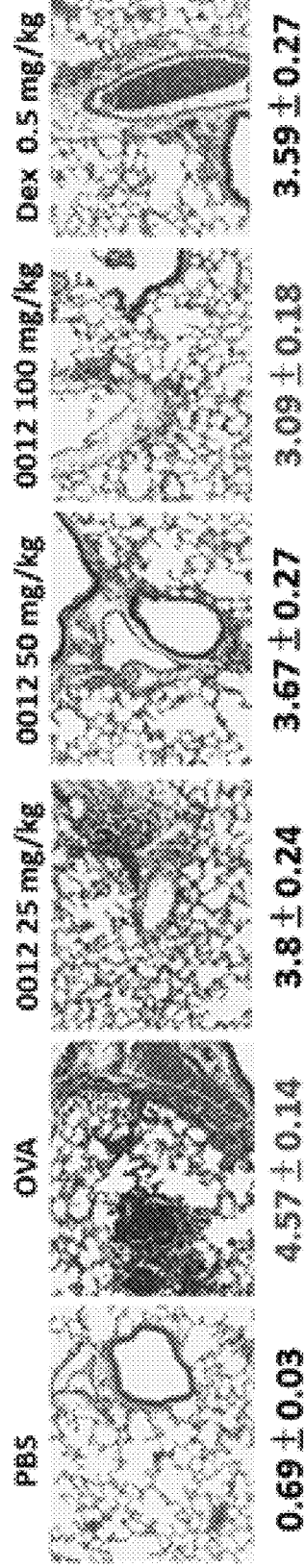
FIG. 3 shows the antifibrotic effects of TMU-C-0012 and dexamethasone on OVA-induced pulmonary fibrosis in mice.
Figure 3:
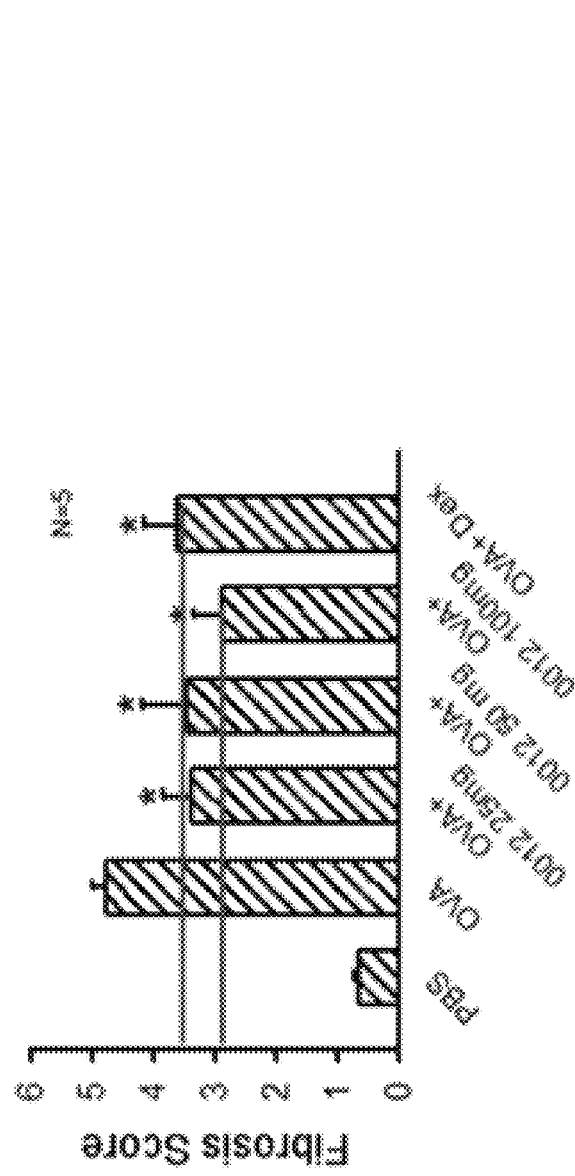

C57BL/6JNarl mice (8 weeks) were treated with OVA (50 μg/50 μl/day) or PBS (50 μl/day) by i.p. injection for 4 weeks. Then, mice were exposure of OVA (5% aerosol exposure) or PBS (aerosol exposure) for 8 weeks. TMU-C-0012 (25 mg/kg/day, q.d.) and dexamethasone (25 mg/kg/day, q.d.) were administered orally to OVA-injected mice from 4 weeks to 12 weeks. On weeks 12, the mice were sacrificed, and the histologic analysis of lung tissue was performed by hematoxylin-eosin (H&E) staining (original magnification, ×100). FIG. 3 shows the antifibrotic effects of TMU-C-0012 and dexamethasone on OVA-induced pulmonary fibrosis in mice. The result suggests that TMU-C-0012 inhibits OVA-induced lung fibrosis in a dose dependent manner, and the efficacy of TMU-C-0012 in inhibition is higher than dexamethasone.

Example 5

Effect of TMU-C-0012 on Silica-Induced Lung Fibrosis in Mice

Figure 4:
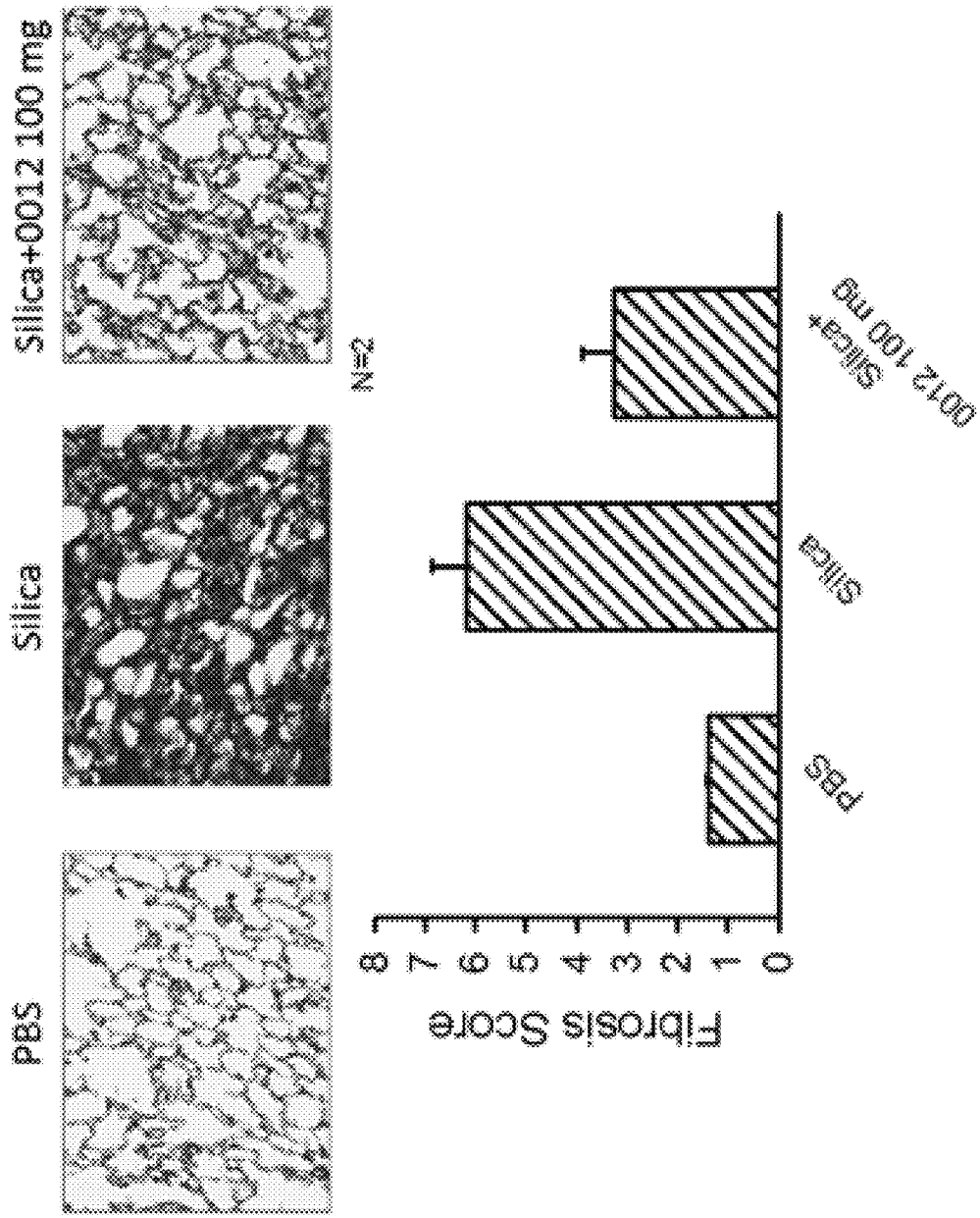
FIG. 4 shows the antifibrotic effects of TMU-C-0012 on Silica-induced lung fibrosis in mice.

C57BL/6JNarl mice (8 weeks) were treated with silica (silica 2.5 mg/50 μl) or PBS (50 μl) by endotracheal administration. TMU-C-0012 (100 mg/kg/day, q.d.) were administered orally to silica-treated mice from 1 to 21 days after BLM treatment. On day 21, the mice were sacrificed, and the histologic analysis of lung tissue was performed by hematoxylin-eosin (H&E) staining (original magnification, ×100). FIG. 4 shows the antifibrotic effects of TMU-C-0012 on silica-induced pulmonary fibrosis in mice.

Example 6

Effect of TMU-C-0012 on CCl4-Induced Liver Fibrosis in Mice

Figure 5:
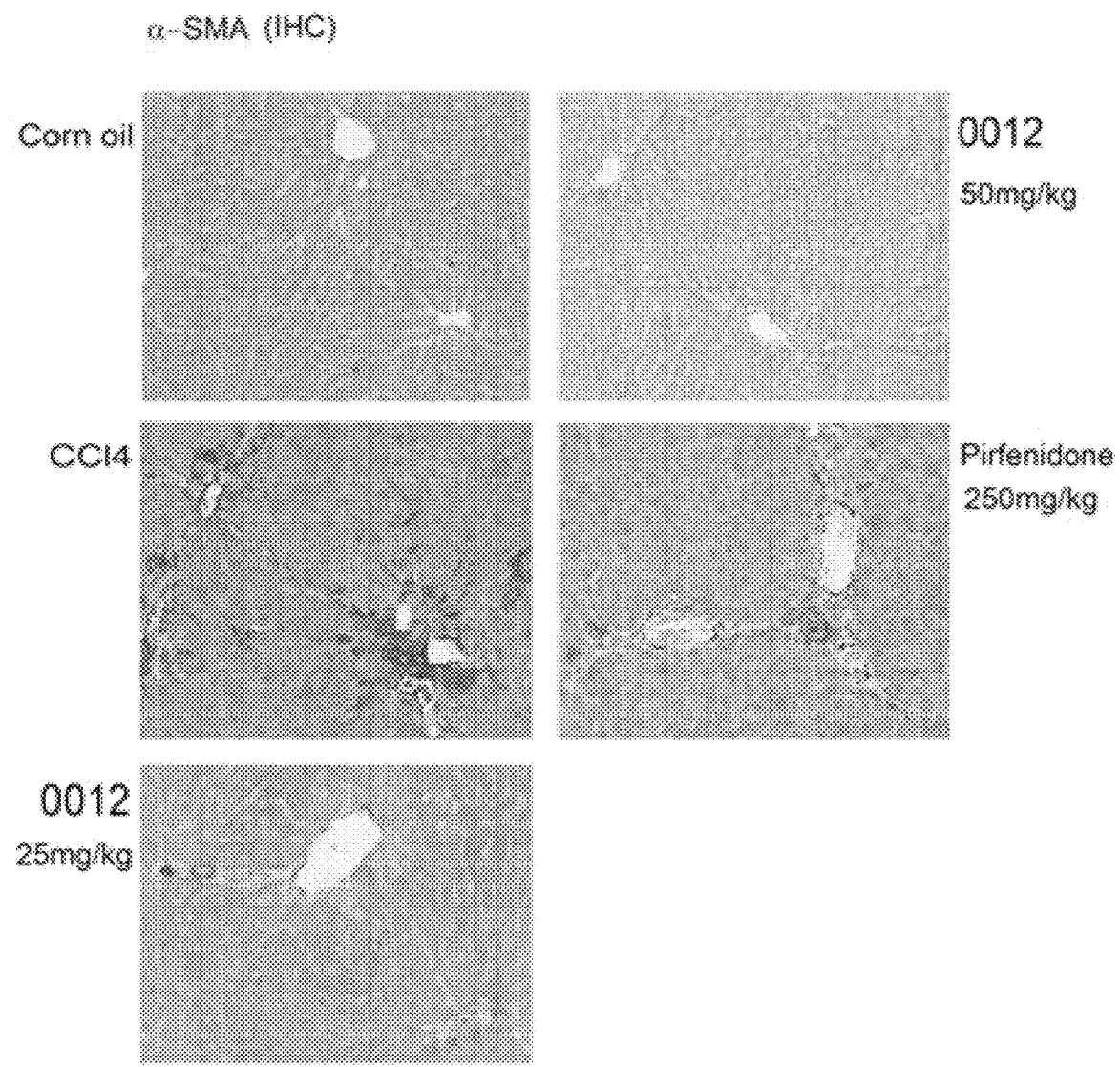
FIG. 5 shows the antifibrotic effects of TMU-C-0012 and pirfenidone on CC14-induced liver fibrosis in mice.

C57BL/6JNarl mice (8 weeks) were treated with CC14 (1 μl/μg/BW, q.w.) or PBS (1 μl/μg/BW, q.w.) by i.p. injection for 6 weeks. TMU-C-0012 (25, 50, 100 mg/kg/day, q.d.) and pirfenidone (250 mg/kg/day, q.d.) were administered orally to CCl4-injected mice from 2 weeks to 6 weeks. On day 43, the mice were sacrificed, and the α-SMA analysis of liver tissue was performed by IHC staining (original magnification, ×100). FIG. 5 shows the antifibrotic effects of TMU-C-0012 and pirfenidone on CCl4-induced liver fibrosis in mice. As shown in FIG. 5, the inhibition of TMU-C-0012 on CCl4-induced liver fibrosis is dose-dependent, and the efficacy of TMU-C-0012 in inhibition is higher than pirfenidone.

We claim:

1. A method for treatment of lung fibrosis, liver fibrosis or renal fibrosis in a subject, comprising administering a pharmaceutically effective amount of a compound of Formula (I) or a pharmaceutically acceptable salt, as an active ingredient to the subject in need thereof;

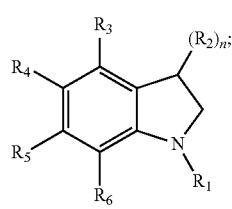

(I)

wherein n is 1, or 2;
$R_1$ is $SO_2R_a$, in which $R_a$ is substituted or unsubstituted phenyl, or heteroaryl;
$R_2$ is —H or $C(O)NR_cR_d$, in which each of $R_c$, and $R_d$, independently, is H, hydroxy, or alkoxy; and
each of $R_3$, $R_5$, and $R_6$, independently, is H, alkyl, alkenyl, alkynyl, CH=CH—C(O)$NR_cR_d$, NHC(O)—CH=CH—C(O)$NR_cR_d$, or C(O)$NR_cR_d$, in which one of $R_c$, and $R_d$, is H, and the other is hydroxyl;
$R_4$ is CH=CH—C(O)NHOH;
or a solvate or prodrug thereof.

2. The method of claim 1, wherein the compound of formula (I) is selected from the group consisting of:

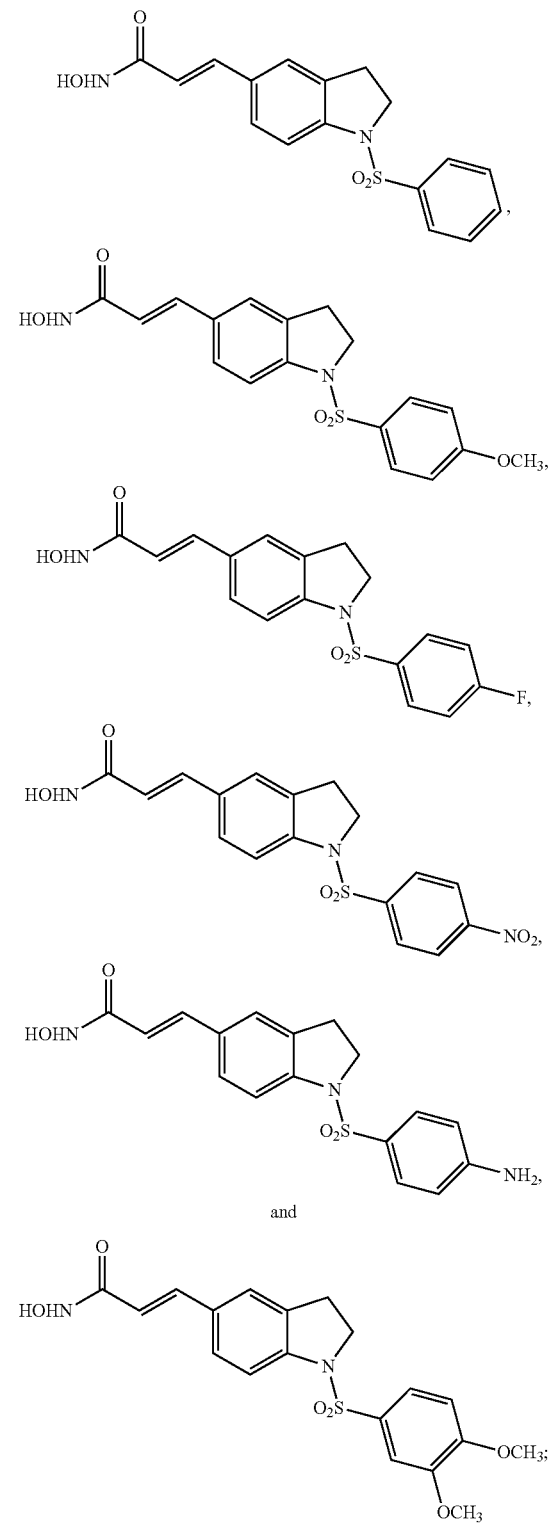

or a pharmaceutically acceptable salt, solvate or prodrug thereof.

3. The method of claim 1, wherein the compound of formula (I) has the following structure:

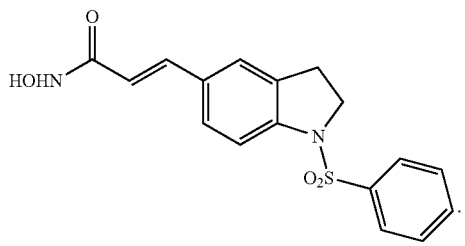

4. The method of claim 1, wherein the effective amount of the active ingredient used in the method of the invention ranges from about 1.5 mg/kg/day to about 20 mg/kg/day.

5. The method of claim 1, wherein the effective amount for treatment is about 5.0 mg/kg/day to about 20 mg/kg/day.

6. The method of claim 1, wherein the effective amount for prevention is about 1.5 mg/kg/day to about 10 mg/kg/day.

7. The method of claim 1, wherein the active ingredient is further co-administered with a second anti-fibrosis agent.

8. The method of claim 7, wherein the second anti-fibrosis agent is pirfenidone, nintedanib, LOXL2 antibody, simtuzumab, IL-13 antibody, lebrikizumab, αVβ6 antibody, CTGF antibody, tipelukast (MN-001), or aerosol pirfenidone (GP-101).

9. The method of claim 7, wherein the co-administration is simultaneous, separate or sequential administration.

10. The method of claim 1, wherein the lung fibrosis is idiopathic pulmonary fibrosis.

11. The method of claim 1, wherein the treatment of lung fibrosis further comprises a co-administered therapy with lung transplantation, hyperbaric oxygen therapy (HBOT) or pulmonary rehabilitation.

12. The method of claim 1, wherein $R_2$ is H.

* * * * *